United States Patent [19]
Wood

[11] Patent Number: 5,700,646
[45] Date of Patent: Dec. 23, 1997

[54] COMPREHENSIVE IDENTIFICATION SCHEME FOR PATHOGENS

[75] Inventor: Sheila J. Wood, Edgewood, Md.

[73] Assignee: The United States of America as represented by the Secretary of the Army, Washington, D.C.

[21] Appl. No.: 530,400

[22] Filed: Sep. 15, 1995

[51] Int. Cl.$^6$ .............................. C12Q 1/68; C12Q 1/70
[52] U.S. Cl. ................................. 435/6; 435/5; 436/172; 935/77; 935/78
[58] Field of Search ................. 435/65, 7.2, 7.1; 536/23.1; 436/501, 518, 164, 172, 805; 935/77, 78

[56] References Cited

U.S. PATENT DOCUMENTS

| | | | |
|---|---|---|---|
| 4,766,062 | 8/1988 | Diamond | 435/6 |
| 5,232,830 | 8/1993 | Van Ness | 435/6 |

FOREIGN PATENT DOCUMENTS

| | | |
|---|---|---|
| 0070685 | 1/1983 | European Pat. Off. . |
| 0330185 | 8/1989 | European Pat. Off. . |

*Primary Examiner*—Carla J. Myers
*Attorney, Agent, or Firm*—Ulysses John Biffoni; John E. Callaghan; Edward Goldberg

[57] ABSTRACT

A method of identifying pathogens, comprising the steps of forming a microsphere having a fluorescent compound attached thereto as a solid matrix for the fluorescent compound. A single strand of DNA is immobilized on the matrix to form a probe, and prior to that a short complementary central piece is formed with a fluorescent compound labelled on one end thereof which joins the central piece to the probe. The two strands bind to form a microsphere/probe complex which is subjected to contact with a complementary strand of an unknown sample to displace the centrally attached probe appendage to provide an increase in fluorescent signal indicative of the emission maxima of the dye in the microsphere to verify the similarity of the unknown sample with known members of the complex. It will be noted that transfer of resonant energy between the complex and the unknown sample identifies the presence of an antigen an adhesin or an antibody, the transfer occurring by use of two fluorescent compounds, one of which absorbs energy at substantially the same wavelength as the other emits energy. Similarly, the presence of a particular sequence of DNA in the unknown sample is determined by fabricating the complementary strand, lysing the organism, splitting the strand of DNA and mixing the resulting probe with the unknown sample, whereby junction of the two strands is affirmed by a chemical signal from the fluorescent dye.

2 Claims, 1 Drawing Sheet

Excite λ A + B
Read λ Em A

Complementary strand present in sample

Increase in signal

COMPREHENSIVE IDENTIFICATION SCHEME FOR PATHOGENS

GOVERNMENT INTEREST

The invention described herein may be manufactured, used, and licensed by or for the United States Government.

This application is a substitute of application Ser. No. 07/773,371, filed Oct. 8, 1991.

FIELD OF THE INVENTION

The present invention relates to classification of microorganisms, and more particularly to a comprehensive identification scheme for pathogens.

BACKGROUND OF THE INVENTION

The taxonomic classification of microorganisms has historically relied on biochemical profiles. The use of or inability to use a selected battery of biochemicals has been the basis for naming and classifying microorganisms. Percent positive and negative reactions from an established organism data base provides the basis for comparison of unknown organismal biochemical patterns. Supplemental tests include gas-liquid chromatography for anaerobes and some non fermenters, immunological tests for antigen identification, and fluorescent tagged antibody for microscopic identification.

Although these methods satisfy the requirement for microorganism identification in a clinical laboratory, they fail to be useful in a situation in which the biochemical utilization patterns of the organisms have been altered as a result of genetic manipulation. Engineered organisms often exhibit a nonsense biochemical pattern which may no longer mimic the stable pattern once used to classify the organism. Organisms such as this would no longer be identifiable by classic methods of taxonomic categorization.

Bacteriological identification has, until the present time, centered around the use of biomass taken from growth on conventional laboratory media for use in an additional battery of prepared biochemical substrates. Although utilization schemes have been miniaturized, the basis for categorization has not changed. Clinical laboratory isolation media has been designed to place organisms in groups based on information such as gram-stain reaction, the ability to degrade one or more sugars, the ability to use selected compounds as a sole carbon source, and the selective use of peptides instead of carbohydrate fermentation. The availability of this information then allows the appropriate follow through battery of biochemicals for genus and species identification.

If one should choose to identify bacteria immediately, as they are taken from the environment, it is not likely that adequate quantities of biomass could be obtained without enriching for growth. In addition, there are instances in which bacteria taken from the environment will not grow on conventional laboratory media because they have adjusted their metabolic capabilities for use of nutrients within the area immediately surrounding them. Therefore, it becomes necessary to design a detection scheme which has the sensitivity to detect very small numbers of organisms in a sample.

There are a number of biochemical identification kits which generate a profile based on the ability of each organism to produce enzymes that break down chosen substrates. Each scheme may be uniquely different in its design and/or ease of use but the basis for identification utilizes the same premise i.e., that the particular genus and species in question will consistently give a reproducible pattern each time it is isolated from a different patient. These approaches are all based on the organisms' abilities to metabolize nutrients and exchange protons across their membranes. These methods are also applied to organisms collected from the environment after they have been isolated and repropagated for the acquisition of adequate biomass. Walkaway, instrumented systems with identification times of 4–6 hours instead of 12 hours, have attempted to simplify identification procedures in the clinical laboratory but the organism still has to be taken from growth on the plate which takes 10–20 hours to appear, depending on the organism.

Direct specimen tests using agglutination, for pathogens in cerebral spinal fluid and normally sterile body fluids, are useful when enough biomass is present to allow the reaction to occur. Although these tests are useful in emergency situations, definitive identification is still based on growth of the organism on laboratory media. This then allows the confirmatory analysis of susceptibility testing for proper treatment.

No valid instrumented device exists for detecting and/or identifying bacteria directly from body fluids or clinical specimens. Some manual methods which are available include immunofluorescent staining techniques of direct smears, latex agglutination techniques and the gram stain. Even though these methods serve as a screen for the presence of pathogenic bacteria, most specimens are subjected to standard culture techniques for confirmation of identification and determination of susceptibilities.

The requirement for antimicrobial testing makes it imperative that the organism be recovered, and in the event that further testing is required in the area of minimal inhibitory concentrations (MIC's), the organism must be available. Therefore, even though a noncontiguous series of tests are available for use at the bench, a rapid, comprehensive, overall system for immediate identification does not exist. Present definitive capabilities require 18–24 hours for growth of the organisms and at least an additional 4–6 hours for identification and susceptibilities. A general overall time to identification is 24–72 hours after the specimen is placed on laboratory media for pathogen isolation.

In the detection of low numbers of genetically engineered pathogens from the environment, two major concepts of the classical method of identification become obsolete. First, the assumption that an engineered organism will continue to fall into its previously assigned biochemical profile will not necessarily follow if the organism has been manipulated in any way. For example, a strain of *Escherichia coli* which has been altered by a segment of another organism's genome, for example, *Klebsiella pneumoniae* genome segments, may acquire the ability to use citrate as its sole source of carbon which is classically a characteristic of *K. pneumoniae* instead of *E. coli*. The focus must transfer from taxonomically labelling the organism to examining the content of its DNA. Virulence determinants within the genome must be evaluated to determine the pathogenic potential of the organism.

The second working concept which becomes obsolete is the assumption that sufficient biomass will be available to perform biochemical testing on the organism. Even though continuous monitoring and filtration techniques are available to concentrate any bacteria present, small numbers are significant in certain circumstances and require an ultrasensitive detection method for observation.

Another approach which differs from that of the biochemical evaluations, involves the characterization of the cell wall colonization factors present on the outer surfaces of bacteria. These protein or lipid conjugates often form the basis for establishment of the organisms on mammalian mucosal surfaces. If the factors are present on the surface of the organism, or the organism in question possesses the code in its genome for production of such factors, the organism has the selected potential to colonize.

Outer cell wall antigens have been used in direct specimen testing to categorize organisms on the basis of genus and/or species. These antigen-antibody reactions are often valid approaches to the identification of clinical isolates or toxins produced by the organisms. Some clinical isolates, however, change their immunogenic antigens in an attempt to evade immune mechanisms of the host. This of course, could result in the misinterpretation of negative results if the antiboby is directed against an altered antigen which is no longer reactive.

Antigen-antibody reactions can be useful with certain groups of organisms in which the production of outer cell wall components remains consistent due to their production by highly conserved regions of the DNA. Conservation of such regions has been shown across time and geographic locations. In a comprehensive pathogen detection scheme, it is necessary to be able to identify each of the above described portions of potentially pathogenic bacteria. There are no existing methods or instruments available to do each of this in a universal format.

Accordingly, it is an object of this invention to provide a new configuration and format for capture and identification of each of the above biologics, ie., DNA, adhesins, and antigens.

Another object is to allow the detection and quantitation of each biologic in one instrument using a designated number of disposables, depending on the extent of the evaluation required.

Yet another object is to provide for the use of fluorescent dyes contained in microspheres to eliminate the need for unstable reagents or enzymes to thereby eliminate or diminish problems of instability and technical error.

Other objects will appear hereinafter.

SUMMARY OF THE INVENTION

It has now been discovered that the above and other objects of the present invention may be accomplished in the following manner. Specifically, it has been discovered that it is possible to provide a new configuration and format for capture and identification of each of the above biologies, ie., DNA, adhesins, and antigens. The present invention allows for the detection and quantitation of each biologic using one instrument using a designated number of disposables, depending on the extent of the evaluation required. The present Invention provides for the use of fluorescent dyes contained in microspheres to eliminate the need for unstable reagents or enzymes to thereby eliminate or diminish problems of instability and technical error.

The method of the present invention includes identifying pathogens by forming a microsphere having a fluorescent compound inside. A single strand of DNA is immobilized on the microsphere. To form a probe, a short complementary strand with a fluorescent label on one end thereof is complexed as a central piece of immobilized DNA. This forms a microsphere/probe complex.

The complex, in contact with an unknown sample containing a complementary strand of DNA, displaces the centrally attached probe appendage. This results in an increase in fluorescent signal due to displacement of the fluorescent label heretofore responsible for absorbing emission energy of the fluorescent molecules within the microsphere.

Transfer of resonant energy between the fluorescent molecules contained in the microspheres occurs upon agglutination of the microspheres due to the presence of an antigen antibody adhesive or DNA. The transfer occurs by use of two fluorescent compounds, one of which absorbs energy at substantially the same wavelength as the other emits energy. The presence of a particular sequence of DNA in the unknown sample is determined by fabricating a probe complex and introducing single stranded DNA from the unknown organism which displaces the same short complementary strand on the probe on the probe complex resulting in a change in fluorescent signal.

The same signal read can be used for DNA, for antigen-antibody reactions and adhesin-receptor reactions. Antibodies, antigens, adhesins or DNA probes can be immobilized on microspheres which contain different fluorescent dyes, providing a change in emission spectra upon displacement of the quenching DNA probe signal or agglutination of the microspheres.

DETAILED DESCRIPTION OF THE PREFERRED EMBODIMENT

Figure 1:
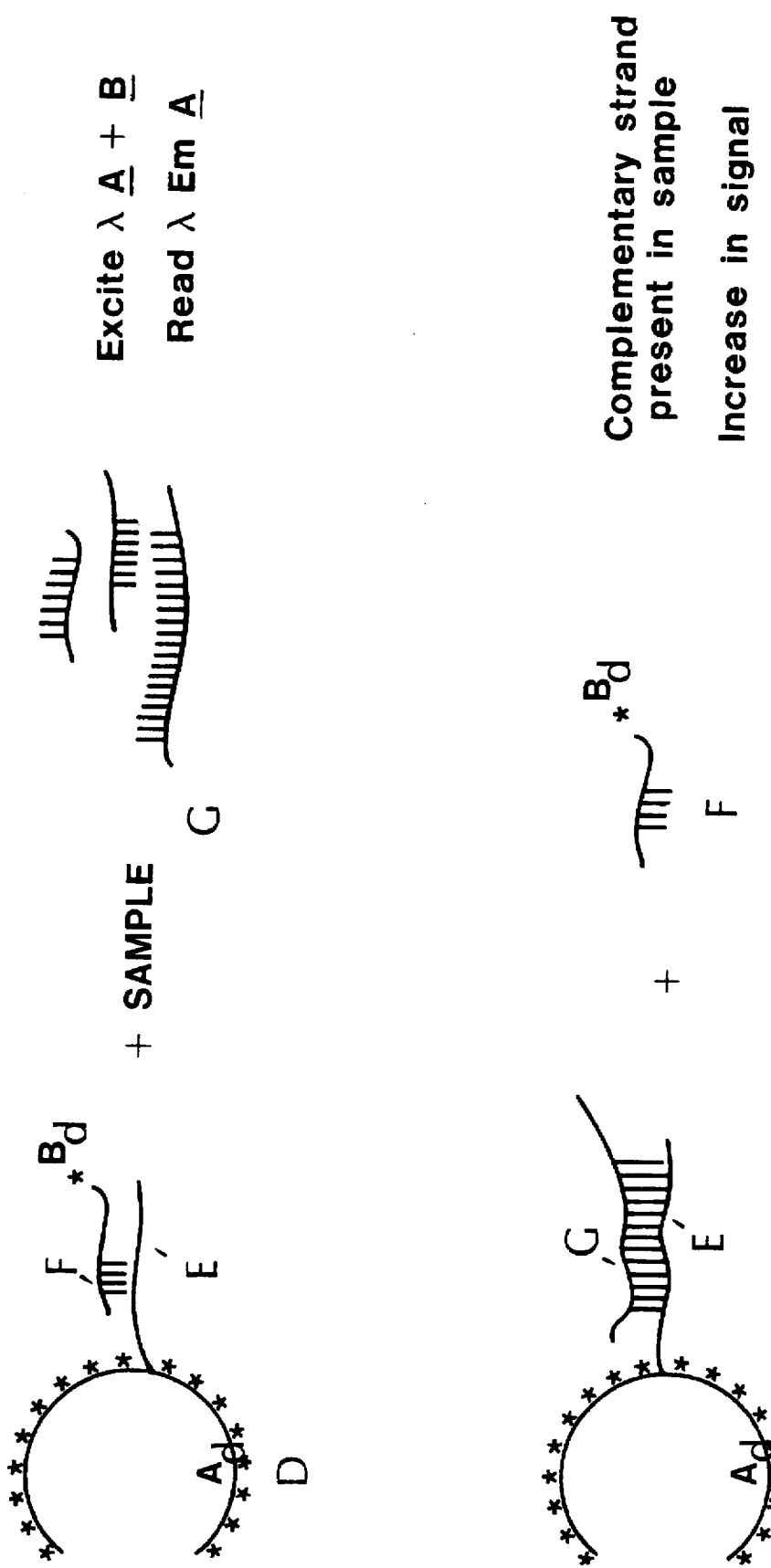
FIG. 1 is a schematic illustration of the DNA hybridization assay of the present invention.

In order to understand the invention in complete detail, reference is made to FIG. 1. FIG. 1 depicts a microsphere containing fluorescent moiety A to which is attached a strand of unlabeled DNA. This strand is annealed to a short complementary strand of DNA to which is attached a fluorescent molecule B which absorbs at the emission wavelength of A. When excited at wavelength A and read at wavelength A, the emission A is quenched as part of its being absorbed by B. This read serves as the baseline read.

When a sample containing a complementary strand larger than the labeled portion is introduced, the signal strand is displaced and quenching diminishes, therefore the signal read of emission A increases. An increase in signal indicates the presence of a strand of DNA complementary to the initial unlabeled strand placed on the sphere A. Thus, specific DNA can be targeted.

The use of two different dyes serves as a built in control for quenching by the sample and will provide an added advantage in the area of sensitivity. The design does not limit the user to only one type of instrumented read. Possibilities exist for a visual read, measurement of an increase in optical density, an increase in biomass, and a colorimetric (spectrophotometric read).

DNA hybridization depends on the successful coupling of two complementary strands of DNA. The presence of a particular sequence of DNA in an unknown organism can be determined by fabricating a complementary strand, lysing the organism, splitting the DNA and mixing the probe with the organism. If the two strands join, an employed chemical signal affirms this coupling. The probe portion of the DNA molecule will be constructed and attached to a micro-sphere containing a fluorescent dye. Attached to this probe will be a complementary DNA strand located in a small central portion of the probe. Onto the end of this central strand will be attached a fluorescent molecule which has an absorption maxima very close to the emission maxima of the fluorescent dye in the microsphere. When the complementary strand in an unknown sample comes in contact with the immobilized probe, the centrally attached probe appendage will be displaced. This will result in an increase in fluorescent signal as the emission maxima of the dye in the sphere is read. The displaced portion serves as a quenching or energy absorbing molecule which, upon displacement, ceases to absorb emission energy from the fluorescing sphere.

The same principle applies to the signal generated when antigen/antibody or adhesin/receptor interactions take place on microspheres. The format or construction of the biologics differs by necessity to conform to the reaction requirements of each, but the basic read principle remains the same. The most sensitive way to construct an antigen/antibody reaction is to perform competitive inhibition assays for the detection of antigen (or antibody) in an unknown sample. The test for antigen would entail planting an antigen onto a microsphere containing fluorescent dye "A". Sample containing unknown antigen is then introduced. A read may be taken at this point to detect possible quenching by sample alone. Next, the counterpart antibody to the antigen in question is added to the reaction mixture. The antibody is planted on a microsphere containing a fluorescent dye "B" which absorbs at the same emission wavelength "A". The degree of quenching that occurs will then be proportional to the amount of agglutination that takes place and hence the amount of antigen in the unknown sample.

Similar antibodies may be placed on microspheres, each containing a different dye. In the presence of antigen, agglutination occurs, and resonance energy transfer is monitored.

The same configuration can be applied to the detection of antibody In sample. The simplest approach would be to plant the antibody on the microsphere containing the dye with the emission spectra to be read. This is not a necessity, however, as the increase in signal can also be monitored following agglutination.

Adhesin/receptor interactions can be monitored in the same manner. In this case, the adhesins are the antigens in question in the sample and should be planted on the microsphere containing the dye whose emission spectra will be read.

The oligonucleotide probe complex attached to microspheres is placed in a contained reaction chamber and packaged for use in a disposable format. The processed sample is then introduced to the reaction mixture and an immediate baseline reading is obtained. This baseline reading will alert the user in the case of prohibitive quenching by the sample diluent indicated by an unacceptable decrease in signal. Binding is then allowed to proceed for a specified time (5 min) and a reading taken. If the signal shows a significant increase, the quenching strand has been displaced and the sample contains strands complementary to the ones attached to the microsphere.

Microspheres can be immobilized to the surface from which the signal is read or can be free in solution. The need for a separation step is obviated when the signal is read from a surface containing immobilized particles. Target nucleotide sequences displace the attached partial strand containing quenching dye and an increase in fluorescent signal results.

Either the antigen (adhesin) portion of the reaction mixture may be immobilized on a solid phase at the read interface or the antibody may be immobilized. Whichever microsphere is immobilized must contain the dye whose emission spectra will be read. A positive sample will result in an increase in signal as the quenching microsphere dye is displaced by antigen, adhesin, or antibody in the test sample.

The means of reading this proposed assay system include; fluorescence reads, light scatter, optical density, or change in biomass. An example of a waveguide design is given below.

DNA hybridization is a process whereby a pre-made single strand of DNA binds to its complementary single strand found in a sample preparation containing microorganisms which have been lysed and treated to contain single instead of double strands of DNA. The method described in this invention is designed for use in a comprehensive pathogen detection scheme using the same signal read as the antigen-antibody reactions and the adhesin-receptor reactions. The process by which positivity is determined is simplified considerably, compared to present methods, which require addition of chemical reagents or intercalating agents. The most widely used forms of signal recognition require the use of enzymes or pairs of enzymes, enzymes plus luminescent substances, or luminescent substances plus fluorescent markers. One requirement for the comprehensive pathogen detection scheme is that the reagents retain stability for at least a 12 month period and are not sensitive to moderate temperature changes.

Enzymes and luminescent reagents are labile in both respects, whereas some fluorescent compounds are stable under such conditions. The system as outlined requires the addition of no reagents, simply the sample to be analyzed. This is a major difference in comparison to existing systems.

Another important difference is the matrix to which the probe is immobilized. It has been shown that hybridization reactions occurring in liquid mixtures occur more quickly and more efficiently (as more sites are available for binding) than hybridization reactions taking place on nitocellulose paper. The configuration used in this disclosure immobilizes the probe to a sphere so that it can move freely throughout the solution and the probe arm has all sites free to take part in the hybridization reaction. This increases the efficiency of the reaction.

Another projected format of this configuration allows the microspheres themselves to be immobilized to a surface, which again allows free movement of the immobilized probes on the side of the microsphere exposed to the liquid sample. Probes have not been labelled in the fashion outlined in this invention.

Perhaps the most unique and important part of this method is the construction of the probe and its signal. The design targets detection of very small amounts of biomass and uses the obviation of fluorescence quenching as an indication of positivity. Slight increases in fluorescence can be seen in this manner, a reflection of small amounts of biomass. The system also has built-in controls for quenching which could be caused by the sample buffer. An increase in signal is indicative of a positive reaction when the sample preparation is measured against a blank of buffer alone.

No other systems have been constructed using the format as described here. Although the probe itself requires significant preparation, once it is placed in the system or immobilized to a surface, no further processing is needed, aside from addition of unknown sample. No other system has this inherent simplicity built into the design of the probe.

For purposes of clarity, the complex will be described fully. A microsphere containing a fluorescent compound is used as a solid matrix to which a probe (single strand of DNA) is immobilized. This first strand requires no chemical labelling. This makes the preparation of the probe and its immobilization much easier. The next step is to place a short complementary central piece of DNA which has been labelled with a fluorescent compound on one end in the reaction mixture. When the two strands bind, the probe is then ready for use.

The principle upon which the method is based is resonance energy transfer. This process uses two fluorescent compounds, one of which absorbs energy at the same or a very similar wavelength as the other emits energy. The microsphere/probe complex, when excited at a selected wavelength and read at a selected wavelength will exhibit resonance energy transfer. The interruption of this process is what gives the signal for positivity.

To further explain the present invention, the following experiment was performed. A fluorescent compound with an absorption wavelength of 550 nm and an emission wavelength 590 nm was contained in the sphere to which the probe was attached. The complementary short piece of DNA bound to the probe had a fluorescent label with an absorption wavelength of 590 nm and an emission wavelength of 640 nm. At the excitation wavelength of 550 nm and the read wavelength of 590 nm, the probe itself exhibited a baseline read, reflecting the quenching effect of the label on the short strand which absorbs at 590 nm. Upon introduction of sample, the presence of a longer complementary strand of DNA displaced the short strand, obviating the quenching effect and resulted in an increase in fluorescence. Although examples are spoken of in terms of one probe strand, there are, in fact, a number of strands immobilized to each microsphere.

While particular embodiments of the present invention have been illustrated and described herein, it is not intended to limit the invention and changes and modifications may be made therein without departing from the scope of the following claims.

I claim:

1. A method for the detection of a pathogen in a sample which comprises the steps of:
   (a) providing a reagent complex comprising a solid support labeled with a fluorescent moiety and having attached thereto a single-stranded DNA probe to which is annealed a complementary DNA labeled with a fluorescent quencher;
   (b) contacting the reagent complex with a sample under conditions in which a nucleotide sequence of the pathogen, if present in the sample, hybridizes to the single-stranded DNA probe and displaces the DNA labeled with the fluorescent quencher; and
   (c) detecting an increase in fluorescent signal from the solid support as indicative of the presence of the pathogen in the sample.

2. The method of claim 1, wherein the solid support is a microsphere.

* * * * *